United States Patent
Thorel et al.

(10) Patent No.: US 7,820,148 B2
(45) Date of Patent: Oct. 26, 2010

(54) USE OF A COMPLEX NUTRITIONAL BASE IN COSMETICS, IN PARTICULAR FOR THE HAIR

(75) Inventors: Jean-Noel Thorel, 3 Rue La Rochelle, Paris (FR) 75014; Hugues Gatto, Saint Paul (FR)

(73) Assignee: Jean-Noël Thorel, Paris (FR)

( * ) Notice: Subject to any disclaimer, the term of this patent is extended or adjusted under 35 U.S.C. 154(b) by 0 days.

(21) Appl. No.: 11/820,750

(22) Filed: Jun. 20, 2007

(65) Prior Publication Data

US 2007/0248559 A1    Oct. 25, 2007

Related U.S. Application Data

(63) Continuation of application No. PCT/FR2005/003228, filed on Dec. 21, 2005.

(30) Foreign Application Priority Data

Dec. 21, 2004    (FR)    .................... 04 13658

(51) Int. Cl.
*A61K 8/00*    (2006.01)

(52) U.S. Cl. .................... 424/70.1; 435/404

(58) Field of Classification Search .............. None
See application file for complete search history.

(56) References Cited

U.S. PATENT DOCUMENTS

| | | | | |
|---|---|---|---|---|
| 3,997,559 | A * | 12/1976 | Coirre et al. ............. | 548/403 |
| 5,182,269 | A * | 1/1993 | Gazzani ................ | 514/44 A |
| 5,597,575 | A | 1/1997 | Breitbarth et al. | |
| 5,739,033 | A * | 4/1998 | Soon-Shiong .......... | 348/678 |
| 6,072,030 | A * | 6/2000 | Bombardelli et al. ..... | 530/350 |
| 6,146,664 | A * | 11/2000 | Siddiqui ................. | 424/489 |
| 6,506,732 | B1 * | 1/2003 | Amiot .................... | 514/17 |
| 7,371,396 | B2 * | 5/2008 | Ghisalberti ............. | 424/401 |
| 2002/0034499 | A1 * | 3/2002 | Thorel et al. ............ | 424/93.7 |
| 2003/0049220 | A1 * | 3/2003 | Bailey et al. ............ | 424/70.1 |
| 2004/0146482 | A1 * | 7/2004 | Pauly et al. ............. | 424/74 |

FOREIGN PATENT DOCUMENTS

| | | |
|---|---|---|
| EP | 0107885 | 10/1983 |
| EP | 0383467 | 8/1990 |
| EP | 0572167 | 12/1993 |
| FR | 2535201 | 5/1984 |
| FR | 2694692 | 2/1994 |
| FR | 2864445 | 7/2005 |
| WO | 96/21421 | 7/1996 |

OTHER PUBLICATIONS

Trüeb, R.M., Experimental Gerontology, 2002, vol. 37, p. 981-990.*
Amiot et al. International Dairy Journal vol. 14, 2004 p. 619-626.*
Health Canada, F& DA list, p. 25, CAS No. 84082-51-9.*
Stamatiadis et al., British Journal of Dermatology, 1988, vol. 119, p. 627-632.*
Smithers et al., J Dairy Science, 1995, vol. 79, p. 1454-1459.*
Thiboutot et al., J Invest Dermatol 1995, vol. 105, p. 209-214.*
Trüeb et al., Dermatology, 2003, vol. 207, No. 4, Abstract.*
Brown et al., J. Invest. Dermatol., 2000, vol. 115, p. 849-859.*
USBiological Technical Data Sheet of MCDB 153 Media.*
MPC—Milk Peptide Complex documentation of CLR Chemisches Laboratorium, Jan. 28, 2003.

* cited by examiner

*Primary Examiner*—Leon B Lankford
*Assistant Examiner*—Kade Ariani
(74) *Attorney, Agent, or Firm*—Hueschen and Sage

(57) ABSTRACT

The invention concerns a non-therapeutic treatment of the hair and/or the scalp for men and women, wherein it consists in locally applying at the surface of the scalp a complex nutritional base in aqueous medium, comprising at least one fraction of amino acids, one fraction of water soluble vitamins, one inorganic fraction, including trace elements and metal salts but excluding any cell growth factor and/or any untraceable biological extract of animal or cellular origin.

18 Claims, No Drawings

USE OF A COMPLEX NUTRITIONAL BASE IN COSMETICS, IN PARTICULAR FOR THE HAIR

The present invention relates to a complex nutrient base (abbreviated CNB) in aqueous medium, also called eco-nutritive base, suitable for the treatment of the hair and/or scalp in men or women, and its various uses in the field of hair cosmetics.

In the context of the present invention, "complex nutrient base" means any composition or formulation, in aqueous medium, being distinguished, as described below, from a cell culture medium, in that it excludes any untraced cell growth factor and/or any extract of animal or cellular origin, and approaching a cell culture medium, in that it, by itself, permits a viable in vitro culture of the human epidermal keratinocytes, for example during at least 72 hours, with at least one clonal proliferation on first passage, without living nutritive foundation, such as fibroblasts.

Such CNB have been described in document WO 96/21421, which describes their use, alone or in combination with other components, as an active product or as excipient.

A CNB as considered according to the present invention does not comprise, neither in its original composition nor in its implementation, a growth factor of cellular origin, for example EGF (Epidermal Growth Factor), and/or biological extract of animal or cellular origin.

By virtue of their nature, not only do these extracts have a variable, even indeterminate composition, sometimes with a poorly defined biological origin, and therefore untraceable or untraced, but also certain components are indeterminate as to their exact chemical, indeed biochemical structure.

A CNB as considered according to the present invention comprises no biological extract such as fetal calf serum (FCS) or any bovine pituitary gland extract, untraceable or untraced.

In the context of the present invention, "trace" or "traceable" means the feature whereby the source and the treatment of a biological material can be established and controlled.

A CNB according to the present invention, for example, comprises no cellular plant or animal biological extract, traceable or not, traced or not.

A CNB considered according to the present invention comprises no medicinal active ingredient, such as an antibiotic.

Such CNB comprise, in addition to the aqueous medium, an amino acid fraction, some of them essential, lower than 0.5%, preferably than 0.35% by weight, a water-soluble vitamin fraction lower than 0.2%, and preferably lower than 0.015% by weight, and an inorganic fraction, including trace elements and metal salts, lower than 5%, and preferably lower than 2% by weight, the balance of the composition being represented by water.

Preferably, a CNB according to the invention is entirely formulated in the aqueous phase, using chemical, biochemical and biological entities, whereof the structure of which is identified, for example nomenclatured or listed, so that the chemical composition of the CNB is strictly defined.

A CNB according to the invention results from a human action, and therefore cannot be treated as any natural and/or biological extract obtained, for example, by fractionation of a biological, animal or plant material, for example.

According to document WO 96/21421, such a complex nutrient base has, for example, the following composition, according to Table 1 below:

TABLE 1

| COMPONENTS | Concentration in mg/l | |
|---|---|---|
| Water | q.s.p. | |
| Amino acids | | |
| L-Alanine | 9.2 | |
| L-Arginine HCL | 421.4 | |
| L-Asparagine (anhydrous) | 14.2 | |
| L-aspartic acid | 4.0 | |
| L-Cysteine HCl, H$_2$O | 42.0 | |
| L-glutamic acid | 14.8 | |
| L-Glutamine | 1754.4 | |
| Glycine | 7.6 | 2808.3 mg or 0.281% by weight |
| L-Histidine HCl, H$_2$O | 50.0 | |
| L-Isoleucine | 6.0 | |
| L'Leucine | 131.2 | |
| L-Lysine HCl | 54.0 | |
| L-Methionine | 13.5 | |
| L-Phenylalanine | 10.0 | |
| L-Proline | 34.6 | |
| L-Serine | 126.1 | |
| L-Threonine | 24.9 | |
| L-Tryptophan | 9.3 | |
| L-Tyrosine 2 Na 2H$_2$O | 11.7 | |
| L-Valine | 70.3 | |
| Vitamins | | |
| d-Biotine | 0.02 | |
| Folic acid | 0.80 | |
| Nicotamide | 0.04 | |
| D—Ca Pantothenate | 0.30 | |
| Pyridoxine HCl | 0.06 | |
| Riboflavin | 0.04 | 99.49 mg or 0.099% by weight |
| Thiamine HCl | 0.30 | |
| i-Inositol | 0.06 | |
| Sodium pyruvate | 0.04 | |
| Thymidine | 0.30 | |
| Adenine (HCl) | 18.0 | |
| DL-lipoic acid | 55.0 | |

TABLE 1-continued

| Inorganic components | | |
|---|---|---|
| Sodium chloride | 6800.0 | |
| KCl | 112.0 | |
| Na₂ HPO₄ | 9.2 | |
| CuSO₄ 5H₂O | 421.4 | |
| Sodium acetate | 14.2 | |
| D-Glucose | 4.0 | |
| Hepes (piperazine) | 42.0 | |
| Phosphoryl-ethanolamine | 0.06768 | 16474.2 mg to 16483.25 mg or about 1.65% by weight |
| Ethanolamine | 0.04684 | |
| Sodium sulfate | 3.4 | |
| Sodium bicarbonate | 1160.0 | |
| FeSo₄•7H₂O | 1.39 | |
| MgCl₂•6H₂O | 120.0 | |
| CaCl₂•2H₂O | 13.0 to 22.05 | |
| ZnSO₄•7H₂O | 0.144 | |
| (NH₄)₆Mo₇O₂₄•4H₂O | 0.00120 | |
| Na₂SiO₃•5H₂O | 0.142 | |
| MnCl₂•4H₂O | 0.00002 | |
| SnCl₂•2H₂O | 0.00011 | |
| NH₄ VO₃ | 0.00057 | |

EP-A-0 383 467 describes the use of syrup of molasses, issuing from the sugar industry, by local application to the scalp (or other pilary zones) to treat dandruff and prevent hair loss.

A molasses syrup is a natural extract obtained by fractionation or separation using sugarcane, whereof the precise composition remains indeterminate or variable according to its origin, and having a high content, representing at least 5% of the total composition of the syrup, of sugars, that is glucose, sucrose, fructose, and mono-oligosaccharides.

FR-A-2 535 201 describes a cosmetic composition or preparation intended in particular to favor the nutrition of the pilary follicles. The active part of this composition essentially consists of a medium for the in vitro culture of isolated human epithelial cells, supplemented with fetal bovine serum.

As stated above, a cell culture medium, also supplemented with a fetal bovine serum, is not a CNB as considered by the present invention.

According to FR-A-2 535 201, to favor the passage of the nutrient substances from the culture medium through the skin, the cosmetic composition comprises a dermophilic vehicle or support, comprising for example ethyl alcohol, polyalcohols or polyglycols, and emulsifiers, and also rubefacient agents playing the role of local vasodilators.

Such a non "ecological" vehicle support appears to be incompatible with a CNB as considered by the present invention, and essentially consists of water, because it does not satisfy the biological equilibria of the superficial parts of the human body.

U.S. Pat. No. 5,597,575 describes a topical medicinal composition, for stimulating the regrowth of the hair, comprising as active ingredient one or more liposoluble vitamins, such as vitamin D3 (or some of its active metabolic derivatives), preferably fixed to uncharged inorganic microparticles.

Similarly to Minoxidil, an active ingredient tested below and which is a local vasodilator, the action mechanism of this composition results from irritation caused by vitamin D3 to the scalp, irritation causing a superficial vasodilation, which stimulates the growth of the hair stem, because increasing the vascularization of the dermal papilla favors the input of nutrients to the cells of the matrix of the hair follicle.

However, such a vasodilator effect, generated by the irritating action of the active ingredient, is always accompanied by a slight local inflammation, which is unacceptable in a cosmetic treatment.

It is the object of the present invention to remedy the drawbacks of the previously identified prior art solutions.

In general, it is the object of the invention to adapt a CNB as previously defined, to respond specifically to the nutritional needs of the keratinocytes of the hair follicles or of the matrix of the hair stem (growth zone of the hair stem located above the dermal papilla of the hair follicle).

More particularly, thanks to the local application of a base thereby adapted, the object of the invention is a cosmetic treatment of the hair and/or scalp in men or women, acting by simple contacting of the CNB with the scalp or the hair, and also occurring in addition to or independently of any mechanical action, such as massage of the scalp, favoring the blood irrigation of the root or the vascularization of the follicle, and hence the growth of the hair stem, to the exclusion of any vasodilator effect, increasing the vascularization of the dermal papilla, and by itself, favoring the input of nutrients to the cells of the follicle matrix.

A further object of the invention is a non-therapeutic treatment of the hair and/or scalp favoring the growth of the hair, and stabilizing hair loss, to the exclusion of any other skin activity.

Firstly, the present invention relates to a complex nutrient base in aqueous medium, being distinguished from a cell culture medium in that it excludes any untraced cell growth factor and/or any biological extract of animal or cellular origin, and approaching a cell culture medium, in that, in itself, it permits a viable in vitro culture of an inoculum of human epidermal keratinocytes, with at least one clonal proliferation of said keratinocytes on first passage, without living nutritive foundation, said base comprising, in addition to the aqueous medium, an amino acid fraction lower than 0.5%, and preferably than 0.35% by weight, a water-soluble vitamin fraction lower than 0.2%, and preferably than 0.015%, and an inorganic fraction, including trace elements and metal salts, lower than 5% by weight, and preferably than 2% by weight. According to the invention, said base comprises a sufficient total weight concentration of sulfur-bearing amino acid(s) to permit, in standard in vitro conditions, an increase in the synthesis of keratins of the pilary stem of the hair in men or in women.

Such a CNB may further comprise at least one of the following features, which may be considered alone or in combination:

its total weight concentration of sulfur-bearing amino acid (s) is not higher than 104 mg/l, its total weight concentration of amino acids, including sulfur-bearing amino acids, is between 0.25 and 0.35%, and for example equal to about 0.326%, the weight concentration of the vitamin fraction is between 0.005 and 0.011%, its weight concentration of organic components, including trace elements and metal salts, is between 1.25 and 1.35% and, for example equal to 1.347-1.348% by weight, its glucose concentration is between 0.1% and 0.6%, and for example between 0.45% and 0.6%, its L-hydroxyproline concentration is between 0.003% and 0.01%, and for example between 0.003% and 0.01%, its ascorbic acid composition is between 0.00001% and 0.001%, and for example between 0.0001% and 0.001%, its concentration of each of the following compounds, that is adenosine, guanine, deoxyribose and ribose, is between 0.000001% and 0.0001%, and for example between 0.00001% and 0.0001%, it comprises a cosmetically active quantity for at least one type I 5α-reductase enzyme inhibitor, the type I 5α-reductase enzyme inhibitor comprises a zinc salt, for example zinc sulfate, and/or vitamin B6, the complex nutrient base comprises a total quantity of calcium of between 0 and 22.05 mg/l, and preferably of between 5 and 15 mg/l, the complex nutrient base comprises peptides, for example extracted from milk, in a concentration of between 0.01 and 1% by weight, the pH of the aqueous phase is adjusted to between 7.4 and 7.5, the osmolarity of the aqueous phase is adjusted to between not more than 300 and 350 µOsm.

It is therefore an object of the present invention to adapt a CNB, as previously considered, to various cosmetic applications, including the treatment of the hair and/or scalp in men or women.

Secondly, the invention relates to a cosmetic composition for local use, in particular for the treatment in men of the hair and/or scalp, comprising a CNB as previously defined.

Thirdly, the present invention relates to the use of a CNB as previously defined, for fabricating or obtaining a cosmetic composition suitable for a non-therapeutic treatment of the hair and/or scalp in men or women.

Fourthly, the invention relates to a method for the non-therapeutic treatment of the hair and/or scalp in men or women, characterized in that it comprises a local application to the scalp surface, of a CNB as previously defined.

Such a method serves to treat androgenetic alopecia in the adult, in men or in women.

Such a method serves to promote the growth of the keratinocytes in the matrix of the hair stem, and thereby favor the growth of the hair, and stabilize hair loss. This method is therefore recommended in case of moderate hair loss, and particularly in case of androgenetic alopecia.

Preferably, the CNB is applied once or twice daily to the scalp of the man or woman treated.

The type I 5α-reductase enzyme inhibiting function of any product, compound or substance or of any active cosmetic quantity thereof, can be characterized or identified by the teaching of the publication:

D. Stamatiadis et al, "*Inhibition of 5α-réductase activity, in human skin by zinc and azelaic acid*" British Journal of Dermatology (1988) 119, 627-632; cf in particular pages 628-629.

According to this characterization method:

the materials used are 1,2[$^3$H]-testosterone, [$^{14}$C]-testosterone, 1α [$^{14}$C]-dihydrotestosterone, and [$^{14}$C]-Δ4-androstenedione, and [$^{14}$C]-androstenediols, and also NADPH;

the in vitro source of the 5α-reductase enzyme consists of samplings of the skin on foreskins of children aged from two to three months;

homogenates of this skin are incubated in the presence of increasing concentrations of [$^3$H]-testosterone and of NADPH, and of the candidate product or substance for inhibition; after addition of the [$^{14}$C] steroids, the metabolites are separated, and the quantities of testosterone and Δ4-androstenedione are determined.

Concerning natural peptides, or peptides of natural origin, usable according to the present invention, fractions or extracts obtained from milk of animal origin are used, referred to below as "Milk Peptide Complex" or MPC, for example the Whey Protein extract (Lactis Proteinum) for No. CAS 84082-51-9 and No. EINECS 281-998-7, fabricated and sold by the firm CLR-Chemisches Laboratorium in West Germany.

This extract has for example the following analytical data:

| | |
|---|---|
| pH (0.5% of MPC powder in $H_2O$) | 5.0-7.0 |
| Loss on dryness (2 h at 102° C.) | 2.0-6.0% |
| Nitrogen (Kjeldahl) | 1.4-1.9% |
| Proteins (Sigma Kit BCA-1) | 11.0-16.0% |
| Lactose (Boehringer Kit) | 65.0-71.0% |
| Lactic acid (+) (Boehringer Kit) | 4.5-8.0% |
| Ash (1000° C.) | 6.0-9.0% |
| Residual fat | <0.5% |
| Electrophoresis (SDS-PAGE) | corresponds |
| Biological activity-$EC_{50}$ (migration test) | 50-500 µg/ml |

Concerning the sulfur-bearing amino acids usable according to the feature of composition (f), their weight concentration for increasing the synthesis of the keratins of the hair stem can be determined by performing the test described according to example 3.

Concerning in particular the treatment of the hair and/or scalp, the implementation of the present invention provides the following decisive advantages:

increasing the growth of keratinocytes in the matrix of the hair stem, thereby favoring the growth or regrowth of the hair and stabilizing hair loss, particularly in case of androgenetic alopecia in the adult, practically no side- or undesirable effect exists, such as delayed hypertrichosis.

In general, in its cosmetic applications, a CNB according to the present invention is particularly simple to use, not greasy or sticky. It is perfectly tolerated locally, and devoid of side- or undesirable effects, such as local irritations, burning or itching, contact eczema, and in certain cases, modification of the blood pressure and heartbeat.

A CNB according to the present invention appears to be devoid of any cytotoxicity, regardless of its concentration in the composition in which it belonged, for example with an excipient.

The present invention is now described, by way of example, with a weight composition according to Table 2.

In particular, below, in its application to the hair, that is, for the treatment of the hair and/or scalp, a CNB according to the invention is compared with a proprietary product having the same indication, but medical, that is, Minoxidil (Common International Denomination).

TABLE 2

| LINE NO. | INTERNATIONAL DENOMINATION COSMETIC NOMENCLATURE INGREDIENT (INCL NAME) | CONCENTRATION In mg/l |
|---|---|---|
| 1 | WATER | q.s.p. (1000 ml) |
| 2 | SODIUM CHLORIDE (CI) | 6085 |
| 3 | GLUTAMINE (AA) | 2043.2 |
| 4 | SODIUM BICARBONATE (CI) | 1160 |
| 5 | GLUCOSE (CI) | 4500 |
| 6 | ARGININE HCL (AA) | 421.4 |
| 7 | SODIUM ACETATE (CI) | 300 |
| 8 | DISODIUM PHOSPHATE (CI) | 284 |
| 9 | LEUCINE (AA) | 131.2 |
| 10 | SERIN (AA) | 136.6 |
| 11 | Mg CHLORIDE (CI) | 120.0 |
| 12 | K CHLORIDE (CI) | 112 |
| 13 | VALINE (AA) | 70.3 |
| 14 | SODIUM PYRUVATE (V) | 55 |
| 15 | LYSINE HCL (AA) | 54 |
| 16 | HISTIDINE HCL (AA) | 50 |
| 17 | CYSTEIN HCL (AA)* | 84 |
| 18 | ADENINE (V) | 24 |
| 19 | THREONINE (AA) | 24 |
| 20 | CA CHLORIDE (CI) | 0 to 22.05 |
| 21 | INOSITOL (V) | 18 |
| 22 | GLUTAMIC ACID (AA) | 29.5 |
| 23 | ASPARAGINE (AA) | 29.2 |
| 24 | METHIONINE (AA)* | 20 |
| 25 | TYROSINE (AA) | 11.7 |
| 26 | PHENYLALANINE (AA) | 10.0 |
| 27 | TRYPTOPHAN (AA) | 9.3 |
| 28 | ALANINE (AA) | 18.1 |
| 29 | GLYCINE (AA) | 15.1 |
| 30 | ISOLEUCINE (AA) | 6.0 |
| 31 | ASPARTIC ACID (AA) | 17.3 |
| 32 | SODIUM SULFATE (CI) | 3.4 |
| 33 | FERROUS SULFATE (CI) | 1.4 |
| 34 | FOLIC ACID (V) | 1.8 |
| 35 | THYMIDINE (V) | 0.73 |
| 36 | CYANOCOBALAMINE (V) | 0.41 |
| 37 | CALCIUM PHANTOTHENATE (V) | 1.3 |
| 38 | THIAMINE HCL (V) | 1.3 |
| 39 | THIOCTIC ACIDE (V) | 0.3 |
| 40 | ZINC SULFATE (CI) | 0.288 |
| 41 | SODIUM SILICATE (CI) | 0.142 |
| 42 | PYRIDOXINE HCL (CI) | 2.1 |
| 43 | NIACINAMIDE (V) | 1.04 |
| 44 | RIBOFLAVIN (V) | 0.4 |
| 45 | BIOTINE (V) | 0.02 |
| 46 | COPPER SULFATE (V) | 0.003 |
| 47 | AMMONIUM MOLYBDATE (CI) | 0.00120 |
| 48 | AMMONIUM VANADATE (CI) | 0.003 |
| 49 | Mn CHLORIDE (CI) | 0.00002 |
| 50 | SODIUM HYALURONATE (CI) | 700 |
| 51 | HYDROXYPROLINE (AA) | 30 |
| 52 | PROLINE (AA) | 46 |
| 53 | ASCORBIC ACID (V) | 1 |
| 54 | ADENOSINE (V) | 0.1 |
| 55 | GUANINE (AA) | 0.1 |
| 56 | DEOXYRIBOSE (CI) | 0.1 |
| 57 | RIBOSE (CI) | 0.1 |
| 58 | "MILK PEPTIDE COMPLEX" (CI) | 200 |
| 59 | CHOLINE CHLORIDE (AA) | 1 |
| 60 | MYO INOSITOL (V) | 2 |

A = Amino acid = 3258 mg = 0.326% by weight *=sulfur-bearing amino acid

V = Vitamin = 109.5 mg = 0.011% by weight

CI = inorganic component = 13466 mg to 13488 mg = 1.347% to 1.348% by weight

EXAMPLE 1

This test concerns Minoxidil, as a reference compound, for then comparing the effectiveness of a CNB of the invention, compared with said reference compound.

The objective of the test is to assess the effect of the Minoxidil (in the form of water-soluble sulfate) on the cellular viability of normal human keratinocytes.

The cellular viability of the keratinocytes is determined by the WST-1(*) conversion technique, which consists in evaluating the activity of the mitochondrial succinate-tetrazolium reductase system of living cells.

The WST-1 (Boehringer/Roche) is reduced to a colored precipitate of formazan. The cellular viability is determined by a spectrophotometric reading at 450 nm. The intensity of the optical density is proportional to the number of living cells.

(*) WST-1 tetrazolium salt: (4-(3-(4-Iodophényl)-2-(4-nitrophényl)2H-5-tetrazolio)-1,3-benzene disulfonate).

The following results were obtained:

Up to the concentration of 0.01%, no cytotoxic effect of Minoxidil is observed after 24 to 48 h of contact. A stimulation of cell growth was even observed at the concentration of 0.001%.

Above this, a sudden cytotoxic effect was observed above 0.1%, with a similar intensity for the 3 highest concentrations.

The following method was used:

Seeding

The keratinocytes were seeded in 96-well microplates at the rate of 20,000 cells per well in 200 µl of KSFM standard culture medium (In Vitrogen). The plates were incubated for 24 h at 37° C. in humid atmosphere containing 6% of $CO_2$.

Concentration Range Tested

The various concentrations to be tested were prepared using a stock solution of Minoxidil (water-soluble sulfate) containing 5% in PBS.

The concentration range tested extended from 0.0001% to 2%.

Treatment

After removal of the KSFM medium, the various dilutions of Minoxidil were contacted with the cells. The media were not renewed during the experiment.

Each point was carried out in quadruplicate.

The cytotoxicity (test with WST-1) was measured after 24 and 48 h of contact.

Analysis

The optical density was read using an ELISA microplate reader at 450 mm.

EXAMPLE 2

The objective of this test was to evaluate the growth of normal human keratinocytes, seeded at low density in the CNB whereof the composition is described in Table 2.

The study was conducted in this CNB, with 0.2 mg/ml of MPC complex (and without MPC complex), versus the standard culture medium of the keratinocytes, KSFM.

The following method was:

The keratinocytes were seeded at low density in 96-well plate in the standard KSFM medium, and grew for 24 h after seeding in this medium.

On the $2^{nd}$ day, the cells were placed in the various media investigated:
  KSFM
  CNB according to Table 2, without MPC complex
  CNB according to Table 2, with MPC complex containing 0.2 mg/ml Each condition was performed in quadruplicate. The media were renewed every three days during the experiment.

The cell density was evaluated 24 h after seeding of the cells, before contacting the various analytical conditions (=T0), and the growth of the keratinocytes was then evaluated on the $2^{nd}$, $4^{th}$, $6^{th}$ and $8^{th}$ days of culture by the WST-1 conversion method (reading at 450 nm).

Cell growth was objectively determined by measuring the cell viability at different experimental times:
  In the presence of MPC complex in a concentration of 0.2 mg/ml, continuous cell growth of the keratinocytes was observed with the CNB according to Table 2.
  Without the addition of MPC complex, no cell growth was observed with the CNB according to Table 2 (in hypocalcic conditions).

In conclusion, in the experimental conditions thus defined, and with a CNB comprising a MPC complex in a concentration of 0.2 mg/ml, regular cell growth of the normal human keratinocytes was observed over 8 days of culture, with an intensity higher than that observed with the same CNB, but without said complex.

EXAMPLE 3

The objective was to evaluate the effect of the CNB according to Table 1 on the proliferation and the differentiation of scalp fragments sustained in survival.

The aim of this test was to determine the efficiency of the base according to Table 1 on the ex vivo survival of human scalp fragments. The proliferation using the Ki67 antibody was evaluated in the outer epithelial sheath surrounding the hair. The differentiation of the keratinocytes using a total anti-cytokeratin antibody was evaluated in the stem of the hair and particularly in its cortical part.

The following materials and methods were used:

1) Survival Maintenance of the Scalp in the Presence of the CNB According to Table 1

Scalp fragments from 5 different donors (patients suffering from androgenetic alopecia, sampled at the junction between the zone where the hair persisted and the alopecia zone) were deposited in inserts, themselves positioned on the culture wells.

Since the CNB contained no preservative, antibiotics were added (fungizone, gentamycin). The effectiveness of the CNB on the survival and differentiation of the skin fragments was compared with that obtained in the presence of a PBS type phosphate buffer. The CNB according to Table 1 versus PBS was added daily to the bottom of the wells, a passage occurring by slow diffusion between the two compartments via a porous membrane (12 μm).

The scalp fragments were maintained in survival in a stove at 37° C. and in an air/5% $CO_2$ atmosphere for 48 hours.

2) Analyses

The scalp fragments were fixed in Bouin's liquid and set in paraffin.

The immunohistochemical evaluation of proliferation was carried out in the outer epithelial sheath surrounding the hair. This outer epithelial sheath is histologically considered as a prolongation of the surface epidermis. Differentiation was evaluated in the cortical part of the hair stem. In fact, the hair stem consists of the central part of the medullary (central column made of non-nucleated cells), of the cortical made of keratinized cells containing melanic pigments and of the cuticle.

a) Immunohistochemical Analysis of Mitotic Activity of the Outer Epithelial Sheath of the Follicles Epithelial proliferation was analyzed by immunohistochemistry using an anti-Ki67 antibody (labelling of cells in phases M, S, G1 and G2 of the cell cycle). Immunodetection was carried out using an indirect immunoperoxidase technique in 3 layers, amplified (DAKO kit) and developed in DAB.

The number of labelled cells was evaluated in the outer epithelial sheath of the root sections present in the scalp (8 to 10 per section). The percentage of cells undergoing proliferation was thereby calculated.

b) Immunohistochemical Analysis and Epithelial Differentiation of the Cortical of the Hair Stem The epithelial differentiation was identified with a total anti-cytokeratin antibody (Novocastra).

Immunodetection was carried out using an indirect immunoperoxidase technique in 3 layers (ABC Peroxidase kit, Vector Laboratories kit) and developed in DAB (Diaminobenzidine).

The intensity of the immunohistochemical labelling was evaluated using the following semi-quantitative scores in all the follicles of the scalp section analyzed:
  negative: score 0–
  slight: score 1
  moderate: score 2
  high: score 3
  very high: score 4

3) Statistics

Statistical analysis was carried out by the Student's test of reduced deviation or paired samples tests. The significance threshold was set at 5%.

The following results were obtained:

a) Immunohistochemical Analysis of Mitotic Activity in the Outer Epithelial Sheath of the Follicles The analysis of mitotic activity is found in Table I below.

Treatment by the CNB according to Table I served to significantly increase the renewal of the epithelial cells ($p<0.05$). In fact, after treatment, 7.6% of the cells of the outer epithelial sheath were labelled by the anti-Ki67 antibody, compared with 2.6% for the scalp treated with PBS. The mitotic index was also analyzed in the surface epidermis.

The results also favor the CNB according to Table 1, with a proliferation index of 6.4% versus 1.1% ($p<0.05$).

b) Immunohistochemical Analysis and Epithelial Differentiation in the Cortical of the Hair Stem The analysis of epithelial differentiation is shown in Table II below.

Epithelial differentiation tends to be better in the scalps treated with CNB according to Table 1, compared with those treated with PBS: the total score obtained was 3.3 against 2.4. No significant difference was obtained, but the individual case analysis served to observe a much better differentiation in 3 cases treated with CNB according to Table 1 of the 5 and unchanged differentiation for one case.

TABLE I

Cell proliferation (immunohistochemistry using the anti-Ki67 antibody): % of labelled cells of the surface epidermis and the outer epithelial sheath of the follicles

|  | epidermis | Outer epithelial sheath |
|---|---|---|
| Scalp + CNB according to Table 1 | 6.4 ± 2.7* | 7.6 ± 1.9* |
| Scalp + PBS | 1.1 ± 0.9 | 2.6 ± 1.9 |

*comparison between CNB according to Table 1 and PBS control: statistically significant difference (unilateral paired Student's test, $p < 0.05$)

TABLE II

Epithelial differentiation (immunohistochemistry using a total anti-cytokeratin antibody) of the cortical of the hair stems

| Scalp + CNB according to Table 1 | 2.4 ± 1 |
|---|---|
| Scalp + PBS | 3.3 ± 0.9 |

In conclusion, treatment with CNB according to Table 1 serves to obtain a statistically significant increase in the mitotic index in the outer epithelial sheath of the hair follicles.

The epithelial differentiation of the hair stem is improved, but without any significant character.

EXAMPLE 4

This test was intended to test the effect of CNB according to Table 2 on the stimulation of the root (cell proliferation) using scalp fragments kept in survival.

According to Example 3, a statistically significant increase in the mitotic index was identified in the outer epithelial sheath after maintenance of the follicles in survival in the presence of CNB according to Table 1.

The aim of the present study is to identify the effectiveness of a CNB according to the invention and according to Table 2, on the stimulation of the root. The cell proliferation, using the anti-Ki67 antibody, was evaluated in the matrix zone of the root (growth zone of the stem), but also in the outer epithelial sheath of the follicle.

The following materials and methods were used:

1) Survival Maintenance of the Scalp in the Presence of a CNB According to Table 2

Scalp fragments from 6 different donors (cervico-facial lift of a non-alopecia subject) were deposited in inserts, themselves positioned on culture wells.

The effectiveness of the CNB according to Table 2 on the survival and stimulation of the roots was compared, on the one hand, with that obtained in the presence of a PBS type phosphate buffer, and on the other, in the presence of a reference compound tested in two concentrations, Minoxidil containing 0.01 and 2% (dilution in PBS buffer), Minoxidil 0.01% being a non-cytotoxic dose on monolayer cultures of normal human keratinocytes, and 2% being the concentration used in vivo in men, for most of the proprietary products marketed for the treatment of alopecia. Containing no preservative, antibiotics were added to all these tested media (fungizone, gentamycin). They were added daily to the bottom of the wells, a passage taking place by slow diffusion between the two compartments via a porous membrane (12 μm).

The scalp fragments were kept in survival in a stove at 37° C. and in an air/5% $CO_2$ atmosphere for 48 hours.

2) Immunohistochemical Analysis of Mitotic Activity in the Root and the Outer Sheath of the Follicle The scalp fragments were fixed in Bouin's liquid and set in paraffin.

The immunohistochemical evaluation of proliferation was carried out in the root and in the outer epithelial sheath surrounding the hair. This outer sheath is histologically considered as the prolongation of the surface epidermis.

Epithelial proliferation was analyzed by immunohistochemistry using an anti-Ki67 antibody (for labelling cells M, S, G1 and G2 of the cell cycle). Immunodetection was carried out using an indirect immunoperoxidase technique in 3 layers, amplified by (DAKO kit) and developed in AEC.

The number of labelled cells of the outer epithelial sheath was counted between the origin of the sebaceous glands and the beginning of the root zone. Furthermore, the labelled matrix cells in the roots were also counted. The percentage of cells undergoing proliferation was thereby calculated compared to the unlabelled cells.

3) Statistics

Statistical analysis was carried out by the Student's test of the reduced deviation or paired samples test. The significant threshold was set at 5%.

The following results were obtained.

a) Immunohistochemical Analysis of Mitotic Activity in the Roots

The analysis of mitotic activity is shown in Table 1 below.

The incubation of scalp fragments in the presence of CNB according to Table 2 causes a significant increase in the mitotic index in the matrix cells of the root (15.2% of labelled cells), compared with the PBS buffer (0.26% of positive cells) or of Minoxidil 0.01% (4.2% of positive cells) ($p<0.05$). The proliferation rate obtained with the CNB according to Table 2 is close to that observed with Minoxidil containing 2% (11.60% of positive cells).

b) Immunohistochemical Analysis of Mitotic Activity in the Outer Epithelial Sheath of the Follicles The analysis of mitotic activity is shown in Table II below.

The incubation of scalp fragments in the presence of the CNB according to Table II causes a significant increase in the mitotic index in the keratinocytes of the outer epithelial sheath of the follicles (22.3% of labelled cells), compared with the PBS buffer (2.6% of positive cells) ($p<0.05$). According to example 3, treatment with a CNB according to Table I already help to significantly increase the renewal of the cells in the outer sheath, but with a much lower efficiency than that measured according to Table II ($p<0.05$). In fact, after treatment, only 7.6% of the cells of the outer sheath were labelled by the anti-Ki67 antibody, against 2.6% for the scalp fragments treated with PBS.

TABLE I

Cell proliferation (immunohistochemistry using the anti-Ki67 antibody): % of labelled matrix cells in the root of the hair follicle

| N = 6 | % |
|---|---|
| Scalp + CNB according to Table 2 | 15.2 ± 6.7*# |
| Scalp + PBS | 0.26 ± 0.6 |
| Scalp + Minoxidil 0.01% | 4.2 ± 2.45 |
| Scalp + Minoxidil 2% | 11.6 ± 8.7 |

*comparison between CNB according to Table 2 and PBS: statistically significant difference (unilateral paired Student's test, $p < 0.05$)
comparison between CNB according to Table 2 and Minoxidil 0.01%: statistically significant difference (unilateral paired Student's test, $p < 0.05$)

TABLE II

Cell proliferation (immunohistochemistry using the anti-Ki67 antibody): % of labelled cells in the outer epithelial sheath of the follicles

| N = 6 | % |
|---|---|
| Scalp + CNB according to Table 2 | 22.3 ± 4.4*# |
| Scalp + PBS | 2.6 ± 2.7 |
| Scalp + Minoxidil 0.01% | 10.2 ± 5 |
| Scalp + Minoxidil 2% | 17.6 ± 7# |

*comparison between CNB according to Table 2 and PBS: statistically significant difference (unilateral paired Student's test, $p < 0.05$)
comparison between CNB according to Table 2 and Minoxidil 0.01%: statistically significant difference (unilateral paired Student's test, $p < 0.05$)
comparison between Minoxidil 0.01% and Minoxidil 2%: statistically significant difference (unilateral paired Student's test, $p < 0.05$).

| N = 5, for reminder | % |
|---|---|
| Scalp + CNB according to Table 1 | 7.6 ± 1.9* |
| Scalp + PBS | 2.6 ± 1.9 |

In this study, a significant increase in proliferation of the keratinocytes is identified in the outer epithelial sheath of the follicles with CNB according to Table 2, compared with Minoxidil 0.01% (10.2% of positive cells) ($p<0.05$). This cell proliferation rate (22.3%) is close to that obtained with Minoxidil 2% (17.6% of positive cells).

In conclusion, with a model scalp fragment maintained in survival, treatment with a CNB according to Table 2 serves to obtain a statistically significant increase in the mitotic index of the matrix cells of the hair root and of the keratinocytes of the outer epithelial sheath of the follicles. The result is far superior to that obtained with a CNB according to Table 1.

The invention claimed is:

1. A complex nutrient base in aqueous medium, said complex nutrient base comprising between 0.01 and 1 weight percent of a Milk Peptide Complex, at least one type I 5alpha-reductase enzyme inhibitor and a sufficient total weight concentration of sulfur-bearing amino acids(s) to support an increase in the synthesis of keratins of the hair and/or scalp pilary stem; and containing less than 0.5 weight percent of an amino acid fraction, less than 0.2 weight percent of a water-soluble vitamin fraction, and less than 5 weight percent of an inorganic fraction including trace elements and metal salts; and excluding any untraced cell growth factor and any biological extract of animal or cellular origin having an indeterminate composition, and wherein the complex nutrient base in aqueous medium permits viable in vitro culture of human epidermal keratinocytes for at least one clonal proliferation on first passage.

2. The complex nutrient base of claim 1, wherein the total weight concentration of sulfur-bearing amino acid(s) is not higher than 104 mg/l.

3. The complex nutrient base of claim 1, wherein the total weight concentration of amino acids, including sulfur-bearing amino acids, is between 0.25 and 0.35 weight percent.

4. The complex nutrient base of claim 1, wherein the weight concentration of the vitamin fraction is between 0.005 and 0.015 weight percent.

5. The complex nutrient base of claim 1, wherein the weight concentration of inorganic fraction, including trace elements and metal salts, is between 1.25 and 1.35 weight percent.

6. The complex nutrient base of claim 1, wherein the composition further comprises glucose at a concentration of between 0.1 and 0.6 weight percent.

7. The complex nutrient base of claim 1, wherein the composition further comprises L-hydroxyproline at a concentration of between 0.003 and 0.01 weight percent.

8. The complex nutrient base of claim 1, wherein the composition further comprises an ascorbic acid composition at a concentration between 0.00001 and 0.001 weight percent.

9. The complex nutrient base of claim 1, wherein the composition further comprises adenosine, guanine, deoxyribose and ribose, at a concentration between 0.000001 and 0.0001 weight percent.

10. The complex nutrient base of claim 1, wherein the type I 5α-reductase enzyme inhibitor is a zinc salt.

11. The complex nutrient base of claim 1, wherein the composition comprises a total quantity of calcium of between 0 and 22.05 mg/l.

12. The complex nutrient base of claim 1, wherein the pH of the aqueous medium is adjusted to between 7.4 and 7.5.

13. The complex nutrient base of claim 1, wherein the osmolarity of the aqueous medium is adjusted to between not more than 300 and 350 μOsm.

14. A cosmetic composition for topically treating hair and/or scalp, comprising the complex nutrient base of claim 1, and a cosmetically acceptable support.

15. A method for treating hair and/or scalp in men or women, comprising topically applying to the scalp surface a complex nutrient base of claim 1.

16. The method of claim 15, wherein the method is to treat adult androgenetic alopecia.

17. The method of claim 15, wherein the complex nutrient base is applied once or twice daily to the scalp.

18. The method of claim 15, wherein the complex nutrient base is in the form of a cosmetic composition.

* * * * *